(12) United States Patent
Schroeder

(10) Patent No.: US 9,883,963 B2
(45) Date of Patent: Feb. 6, 2018

(54) MODULAR ORTHOSIS SYSTEM AND KIT FOR THE FITTING THEREOF

(71) Applicant: Orthopunkt AG, Solothrun (CH)

(72) Inventor: Jan-Hagen Schroeder, Solothrun (CH)

(73) Assignee: ORTHOPUNKT AG, Solothurn (CH)

( * ) Notice: Subject to any disclaimer, the term of this patent is extended or adjusted under 35 U.S.C. 154(b) by 254 days.

(21) Appl. No.: 14/647,440

(22) PCT Filed: Nov. 26, 2013

(86) PCT No.: PCT/IB2013/002645
§ 371 (c)(1),
(2) Date: May 26, 2015

(87) PCT Pub. No.: WO2014/080274
PCT Pub. Date: May 30, 2014

(65) Prior Publication Data
US 2015/0305911 A1    Oct. 29, 2015

(30) Foreign Application Priority Data

Nov. 26, 2012 (DE) ........................ 10 2012 023 028

(51) Int. Cl.
*A61F 5/00* (2006.01)
*A61F 5/01* (2006.01)

(52) U.S. Cl.
CPC .......... *A61F 5/0127* (2013.01); *A61F 5/0113* (2013.01)

(58) Field of Classification Search
CPC .. A61F 5/01; A61F 5/02; A61F 5/0111; A61F 5/0102; A61F 5/0113; A61F 5/0125; A61F 5/0127; A61F 2005/0139
(Continued)

(56) References Cited

U.S. PATENT DOCUMENTS 3,859,991 A * 1/1975 Theodores ............ A61F 5/0113
602/28
4,459,980 A * 7/1984 Perser ................... A61F 5/0113
128/DIG. 15
(Continued)

FOREIGN PATENT DOCUMENTS

DE        19604309 A1    8/1997
DE      102005058999    2/2007
(Continued)

OTHER PUBLICATIONS

Novacheck et al., "Quantifying the Spring-Like Properties of Ankle-Foot Orthoses (AFOs)" J. Prosthet. Orthot., 2007; 19:95-103.

*Primary Examiner* — Kim M Lewis
(74) *Attorney, Agent, or Firm* — Mayer & Williams PC

(57) ABSTRACT

Provided are systems and methods relating to a modular orthosis system for an orthosis of the lower extremity, which modular orthosis system simplifies an individual fit to the respective patient and his loss of function, and, during the course of the therapy, can be fitted with direct consultation of the patient to changed circumstances in an interdisciplinary manner. A particular exemplary advantage of the orthosis system is that the therapist, together with the patient, can test the position of the support spring (dorsal vs ventral, medial vs lateral) and also different spring strengths. Thus, the orthosis can be fitted to the patient in a simple manner.

13 Claims, 10 Drawing Sheets

(58) Field of Classification Search
USPC .................................. 602/27–29, 5; 128/882
See application file for complete search history.

(56) References Cited

U.S. PATENT DOCUMENTS

| | | | |
|---|---|---|---|
| 5,393,303 A | 2/1995 | Shiono | |
| 2004/0102727 A1* | 5/2004 | Smits | A61F 5/0111 602/28 |
| 2007/0135746 A1* | 6/2007 | Korner | A61F 5/0111 602/27 |
| 2008/0300525 A1 | 12/2008 | Shlomovitz | |
| 2009/0198166 A1* | 8/2009 | Shlomovitz | A61F 5/0111 602/28 |
| 2010/0101118 A1* | 4/2010 | Guenther | A61F 5/0111 36/140 |
| 2011/0160630 A1* | 6/2011 | Cerioli | A61F 5/0111 602/23 |
| 2013/0001264 A1* | 1/2013 | Popovici | F41C 33/0209 224/222 |
| 2013/0018294 A1* | 1/2013 | Jones | A61F 5/0106 602/27 |
| 2013/0072841 A1* | 3/2013 | Bader | A61F 5/0111 602/27 |
| 2015/0148725 A1* | 5/2015 | Johnsson | A61F 5/0111 602/16 |

FOREIGN PATENT DOCUMENTS

| | | |
|---|---|---|
| DE | 102010019844 A1 | 11/2011 |
| EP | 1231873 B1 | 8/2002 |
| WO | 2005117772 A1 | 12/2005 |

* cited by examiner

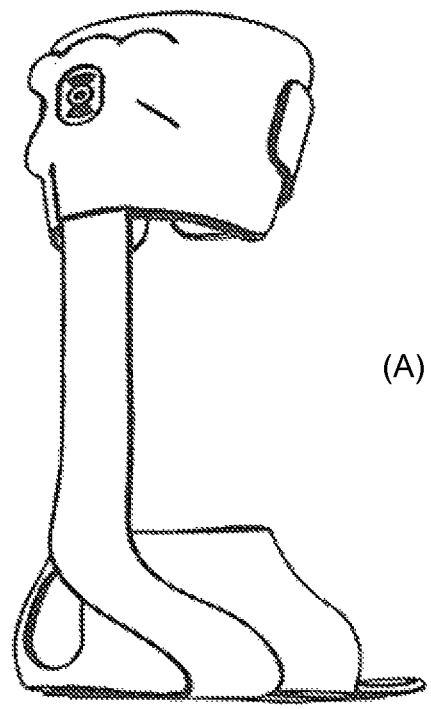
(A)
FIG. 3
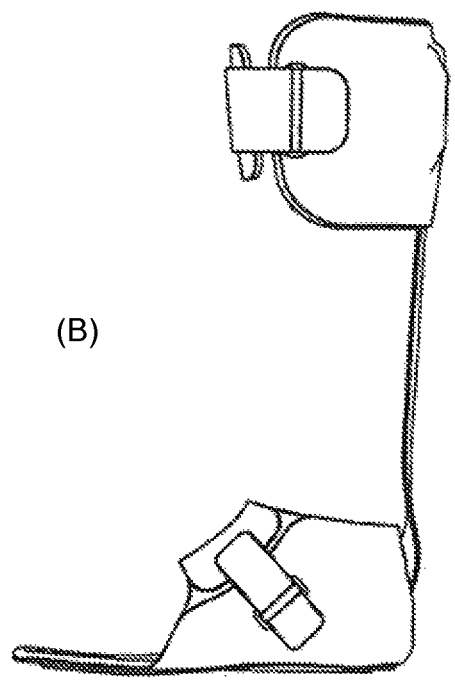
(B)

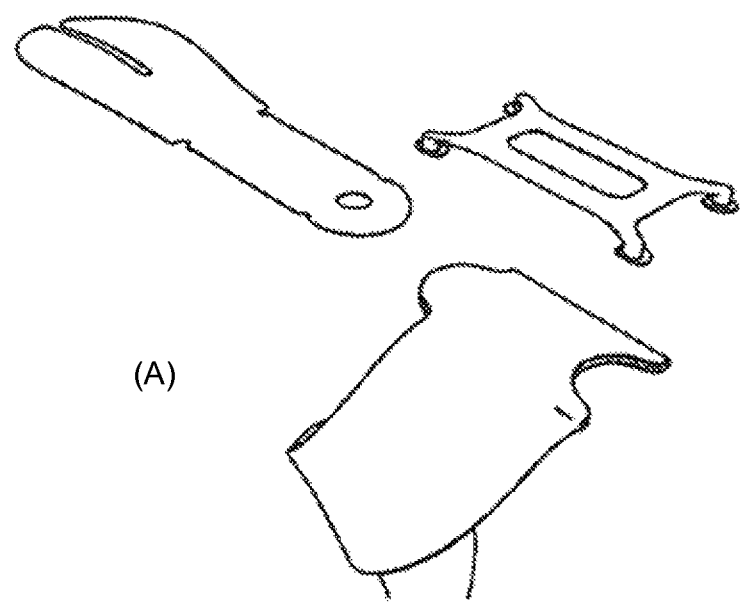
(A)
FIG. 4
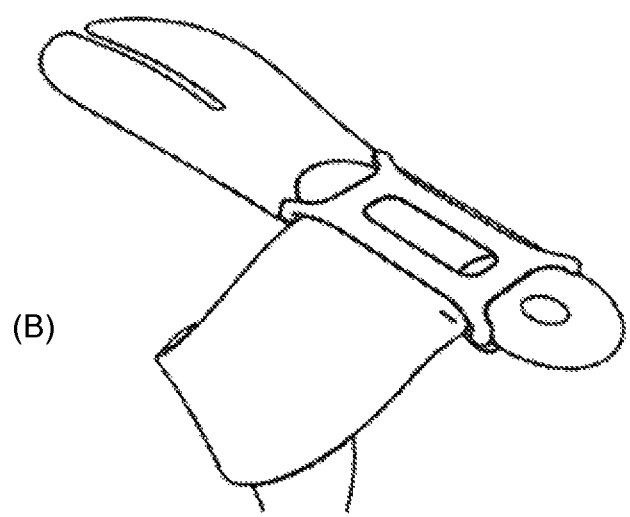
(B)

(A)

(B)

(A)

(B)

(A)
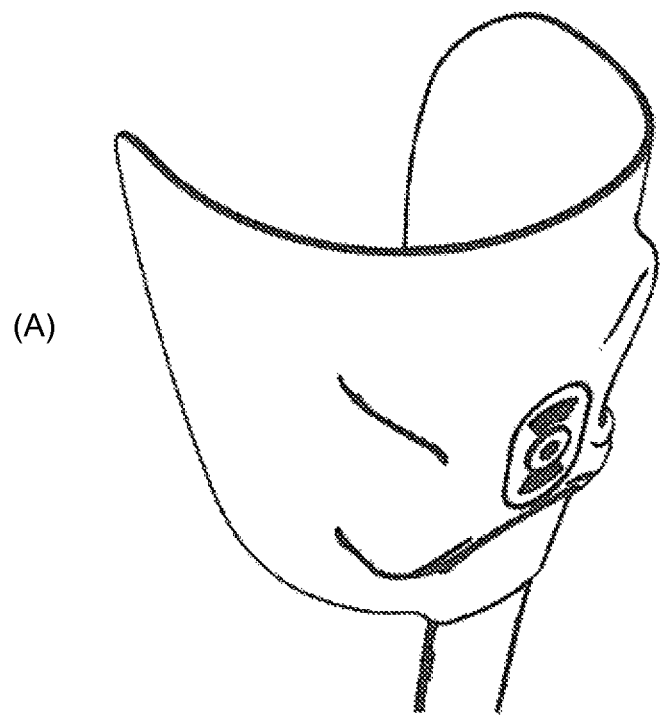
FIG. 7
(B)
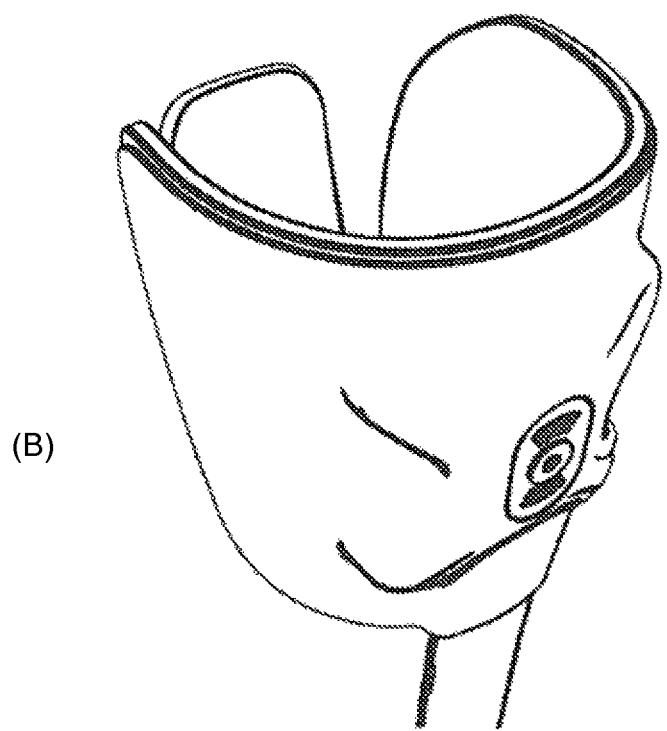

(A)

(B)

(A)

(B)

MODULAR ORTHOSIS SYSTEM AND KIT FOR THE FITTING THEREOF

BACKGROUND OF THE INVENTION

Orthoses are medical means for supporting the limitations of the functionality of extremities, for instance as a consequence of cerebral palsies, foot drop paralyses, strokes, muscular dystrophies, or polio myelitis. Orthoses allow the fixation of body parts to stabilize movements and/or protect and support movement of joints. Orthoses are applied externally on the extremity to be treated and are worn over longer periods of time. Since human anatomy and also the type of restraint can be very different, orthoses need to be adjusted individually to the respective patient. From prior art, orthoses are known that can be adjusted by a variety of adjustment devices. Other orthoses are individually prepared, after exact measurement of the patient's ergonomic conditions, for instance by methods such as "rapid prototyping" or "rapid manufacturing". Nevertheless, it has been found that for many patients it is hardly predictable which exact design is preferable for the orthosis to support the movement behavior in an optimum manner.

For the prior art orthosis systems, individual embodiments have to be determined already before preparation of the orthosis: for instance, for a lower-limb orthosis, it has to be decided whether the support needs to be ventral or dorsal. Usually, the degrees of hardness and the height of sole and support have to be predefined, since a later exchange is not possible. Due to these general conditions, the patient cannot compare different embodiments, such that it cannot be determined whether a certain orthosis represents already the optimum design. Furthermore, without a complete redesign, the common orthosis systems cannot be adjusted to body modifications (e.g., when the patient's body height increases). Usually, compromise solutions are sought due to the cost pressure.

SUMMARY OF THE INVENTION

It is one object of the invention to provide a modular orthosis system for an orthosis of the lower limb, which facilitates an individual adjustment to the respective patient and to his loss of function and which can, in the course of the therapy, quickly be adjusted to different situations.

This object is achieved by a modular orthosis system, comprising a thermally formed sole configured for mounting by reversible form-fit with one or a plurality of preformed receptacles for locking elements, a lower-limb cuff having one or a plurality of fixing devices for fixing at a lower limb, a padding and a receiving device for a backing spring, wherein the backing spring includes an upper flat portion and a lower semicircular portion, the semicircular portion forming a recess for receiving the sole, wherein the backing spring is reversibly connected to the lower-limb cuff, and wherein the backing spring is configured to be attached dorsally/medially, dorsally, laterally, ventrally/medially, or ventrally/laterally at the foot cuff.

BRIEF DESCRIPTION OF THE DRAWINGS

In the following, the invention is explained in more detail with reference to the drawings.

FIGS. 3(A) and 3(B) show an orthosis system according to the invention, wherein the backing spring is disposed dorsally (at the Achilles tendon) in two viewing angles.

FIGS. 4(A) and 4(B) and 5(A) and 5(B) show in a picture sequence details of the attachment of the foot cuff.

FIGS. 6(A) and 6(B) and 7(A) and 7(B) show in a picture sequence the attachment of the backing spring at the lower-limb cuff by means of the connection element according to the invention in an X-shaped design (starfish), including an elastomer with floating screw and padding.

DETAILED DESCRIPTION

The orthosis system according to the invention comprises the following elements: a thermally formed sole with one or a plurality of preformed receptacles for locking elements and optionally a sandal-type foot cuff with padding and fixing devices, a lower-limb cuff with one or a plurality of fixing devices for fixing at the lower limb, a padding and a receiving device for one or a plurality of backing springs, a backing spring with an upper flat portion and a lower semicircular portion, the semicircular portion forming a recess for receiving the sole, the backing spring being reversibly connected with the lower-limb cuff, the backing spring being attachable dorsally/medially, dorsally, laterally, ventrally/medially, or ventrally/laterally at the foot cuff.

The foot cuff is made in the style of a sandal, so that it completely covers the bottom of the foot, but is substantially open toward the top. At least a portion of the cuff extends over the instep, at least another portion of the cuff extends behind the heel, so that the cuff can firmly be fixed at the foot. The foot cuff may be made of any material, which is sufficiently stable (e.g., laminates with Polytol or Orthocryl soft). Preferably, it is a thermoplastically deformable material, which permits smaller adjustments. Foot cuffs according to the invention can be made in standard foot sizes, but may however also be made individually to a plaster cast or with support by a CAD/CAM system. Methods for making such foot cuffs are in principle known.

The foot cuff and the lower-limb cuff may receive an inside padding of washable, heat and humidity-transporting, air-permeable, hook-and-loop-fastenable ("Velcro") 3-D spacer fabric (e.g., Space Tex). In combination with Microklett, the padding can easily be removed and washed.

Figure 1:
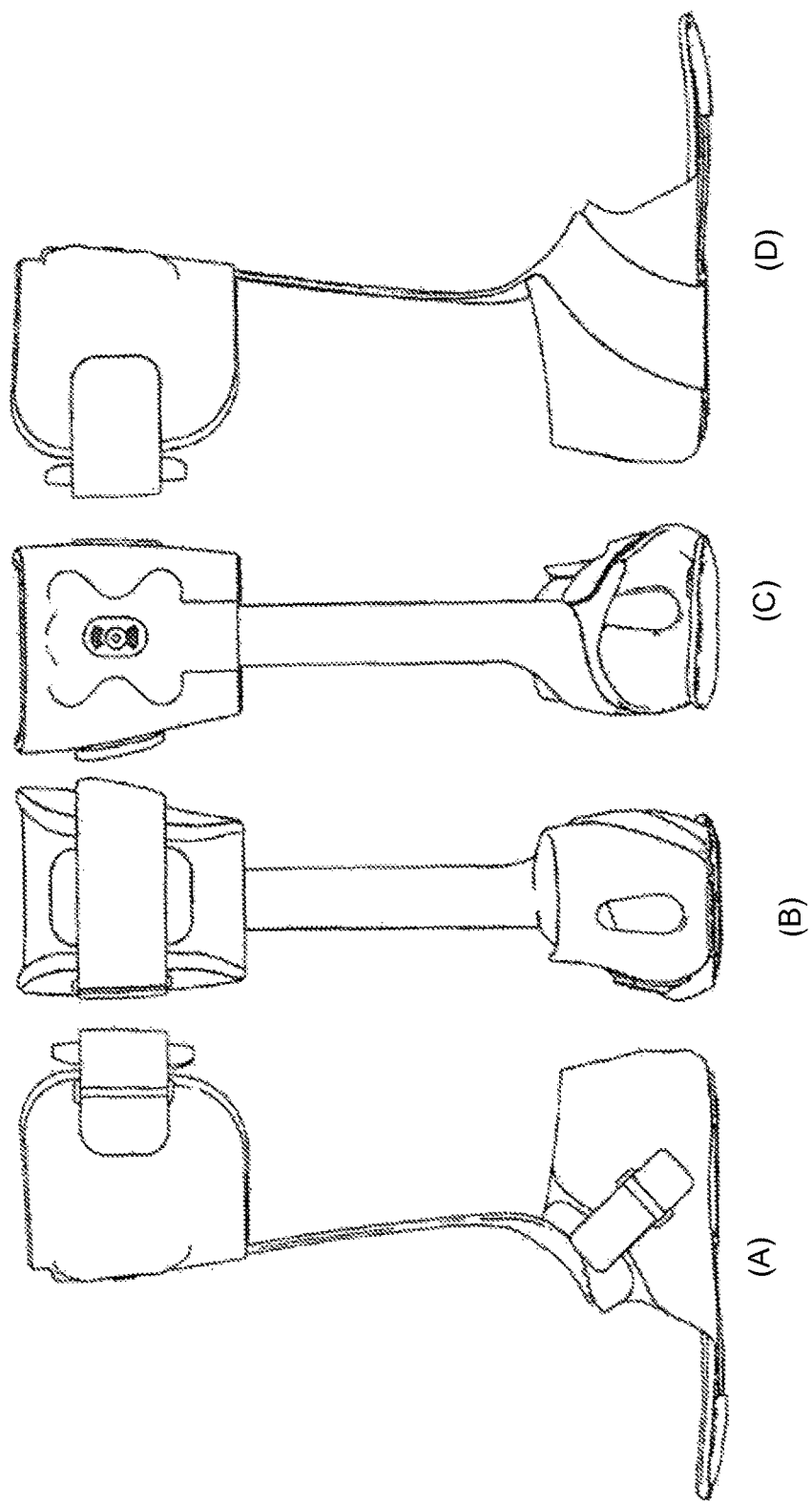
FIGS. 1(A)-1(D) shows a survey of an orthosis system according to the invention in four different viewing angles.
Figure 2:
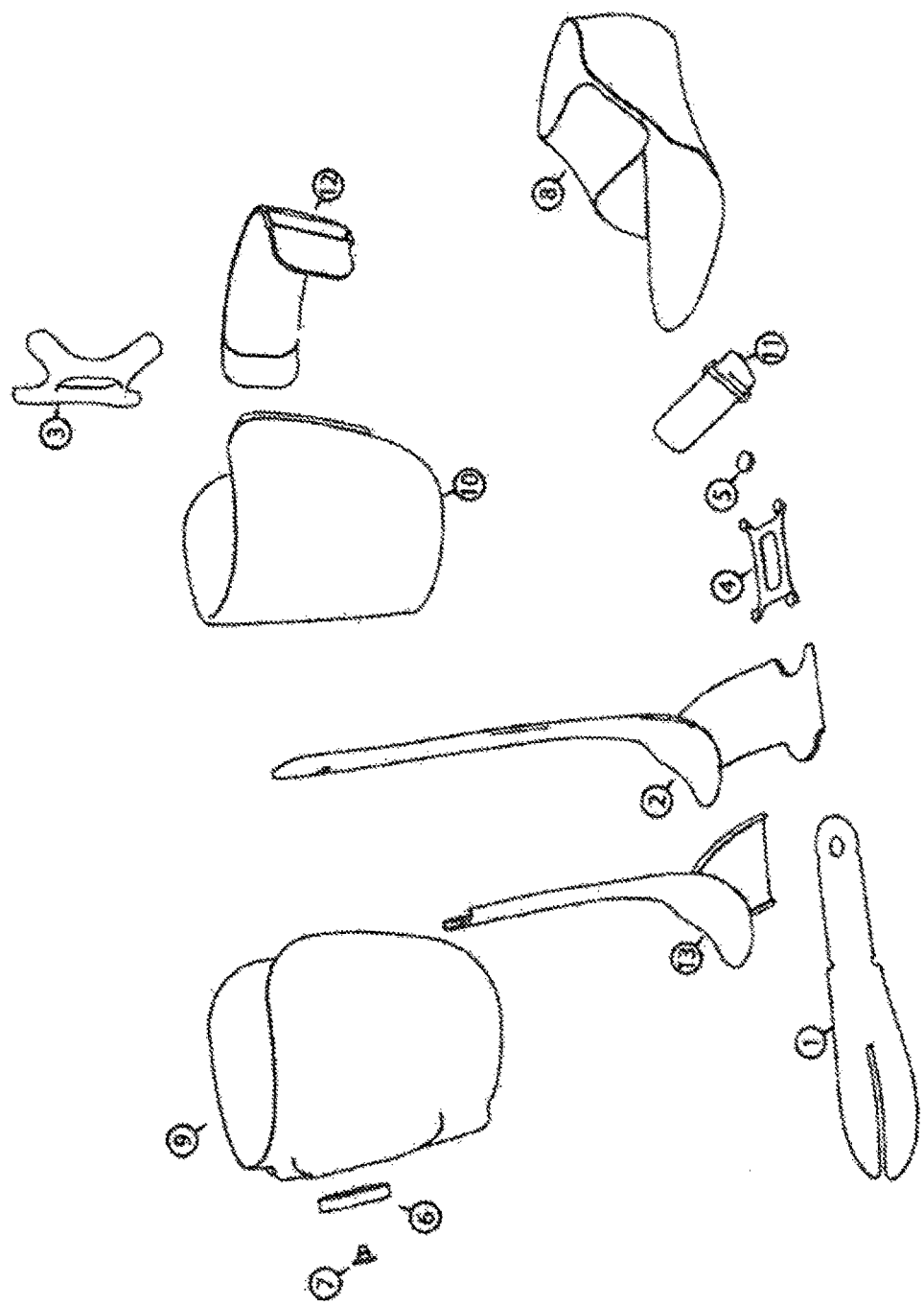
FIG. 2 shows the modular design of the orthosis system according to the invention comprising the following portions:
1: sole
2: backing spring
3: connection element (starfish) with recess
4: sole locking
5: sole locking intensifying afference
6: connection element (elastomer) for starfish recess
7: screw
8: sandal-type foot cuff
9: lower-limb cuff
10: padding
11: closure element (fixing device)
12: closure element (fixing device)
13: optionally additional protection element (bumper) for backing spring
Figure 5:
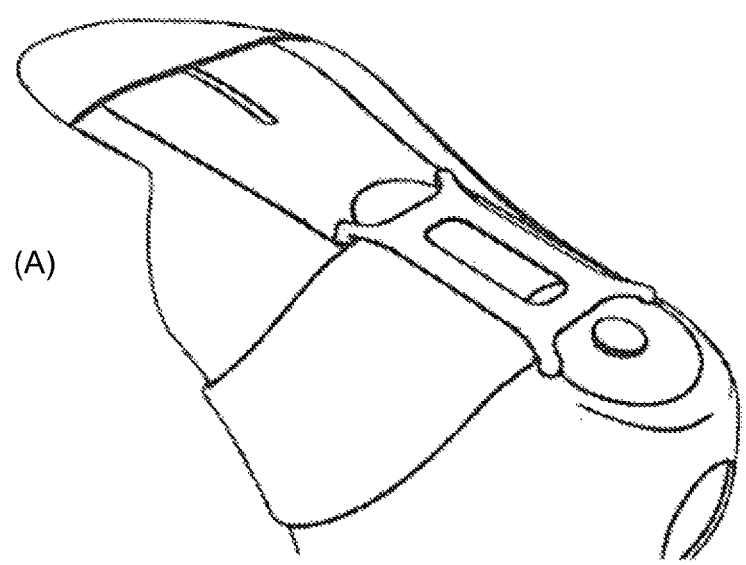
Figure 5:
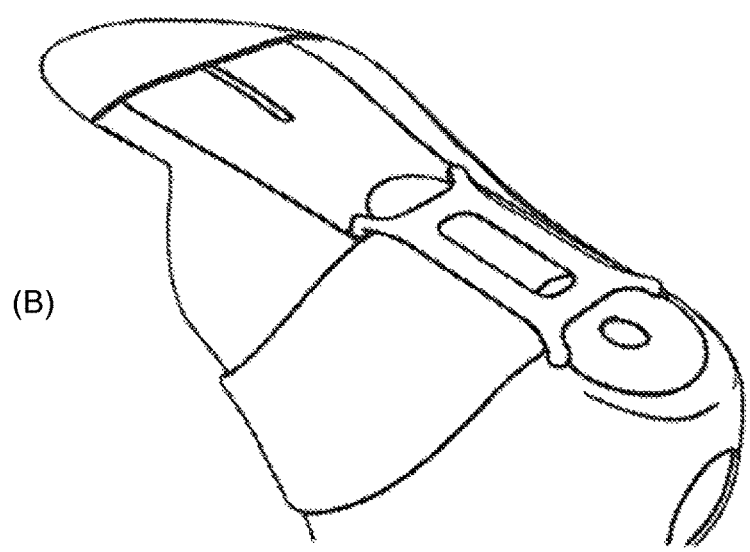
Figure 6:
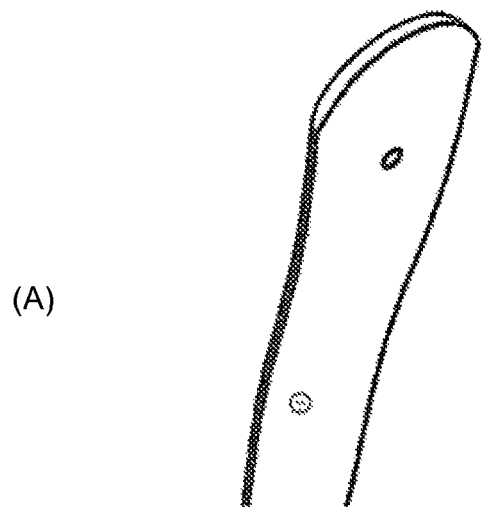
Figure 6:
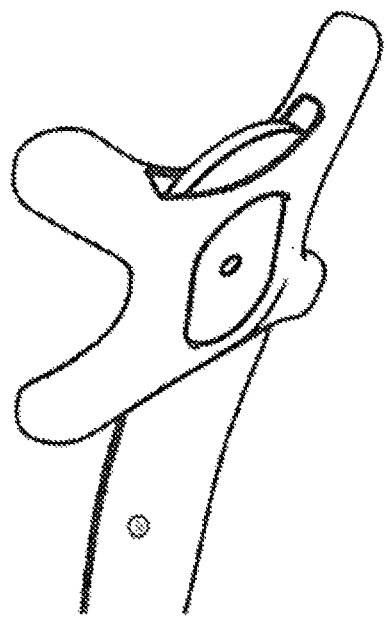
Figure 8:
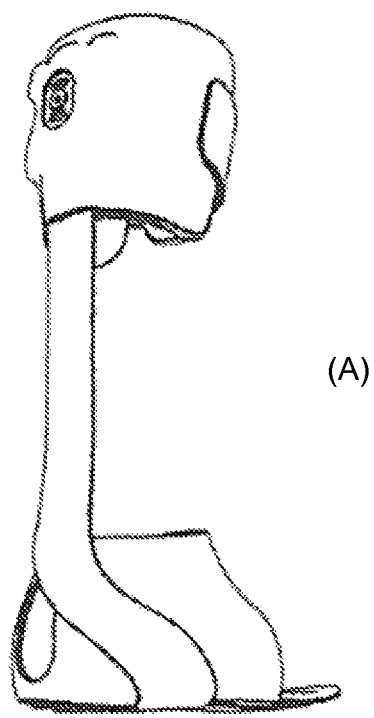
FIGS. 8(A) and 8(B) and 9 show an orthosis system according to the invention with dorsal attachment of the lower-limb cuff.
Figure 8:
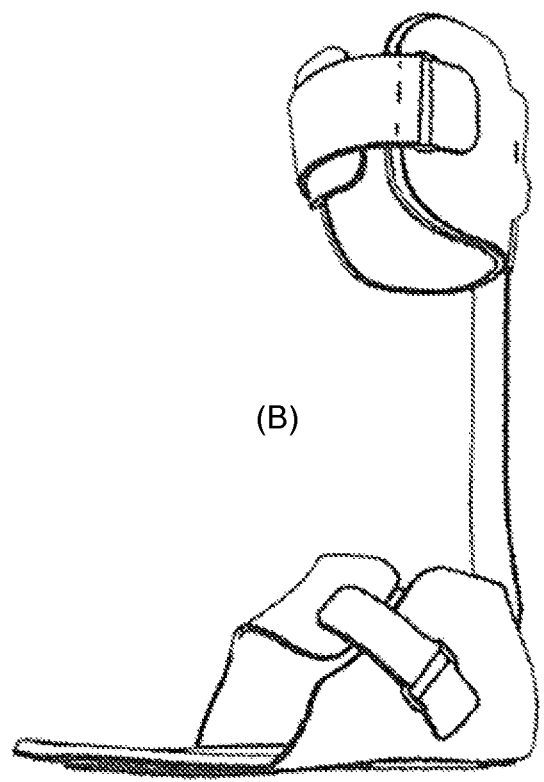

Locking of the sole with the sandal-type foot cuff occurs by using a locking element, which is located centrally beneath the patient's heel (see FIG. 2, No. 5). In the preferred embodiment, this locking element is flexible, but less flexible than the padding, so that the locking element intensifies afferent activity. It has been found that patients with the functional limitations of the lower limbs mentioned above often show perception disorders, too, so that they have perception problems when walking, e.g., when the foot hits the ground, in particular when using an orthosis. These perception problems will lead to further difficulties in the patient's postural control. By using a locking element that intensifies afferent activity, which is preferably located centrally under the patient's heel, the perception of the hitting on the ground is clearly improved, which contributes to another improvement of the patient's postural control. It is understood that the locking element that intensifies afferent activity, has to be designed with respect to the dimensions and the degree of elasticity such that no pressure lesions will occur for the patient.

The lower-limb cuff is U-shaped and substantially encloses the lower limb. It is attached by means of an additional fixing device (e.g., a buckle or a Velcro tape) at the lower limb. In order to cover the different lower limb sizes of different patients, the lower-limb cuff can be offered in standard sizes.

Preferably, it is prepared individually, for instance using a plaster cast. The lower-limb cuff can be made of different materials, provided that the material has a sufficient continuous load capacity (such as, e.g., laminates with Polytol or Orthocryl soft). Preferably, it is a thermoplastic material, which allows smaller adjustments. The lower-limb cuff furthermore includes a padding of washable, heat and humidity-transporting, air-permeable, hook-and-loop-fastenable ("Velcro") 3-D spacer fabric (e.g., Space Tex).

Another important aspect of the invention is the support (web). This support (also called "dynamic web" or "backing spring") substantially is a leaf spring (with an energy-regenerating push-up function), the stiffness of which is adjusted to the individual under special consideration of the body weight, the body height, and the myotonus. Materials, methods for adjusting and methods for measuring the return force are known from prior art (see, e.g., Novacheck et al., J. Prosthet. Orthot., 2007; 19:98-103). The backing spring is introduced at its upper end into a corresponding opening with guidance of the lower-limb cuff and is connected thereto by clamping and screwing in a nearly joint-type manner with a unidirectional floating nut, such as, e.g., the case for a support with an elastomer. At its lower end, it has a semicircular shape, in order to enclose the foot cuff. Further fixing devices have the effect that the foot cuff will not come loose from the backing spring during use. Optionally, the backing spring can be protected at its surface against mechanical damage by a protection element "bumper". This bumper preferably is made of a flexible material, such as rubber and/or silicone. The bumper can be produced in different colors and designs and/or imprinted and/or otherwise provided with patterns. Thus, in addition to the protection function for the material of the backing spring, the bumper also has an esthetic function.

Figure 9:
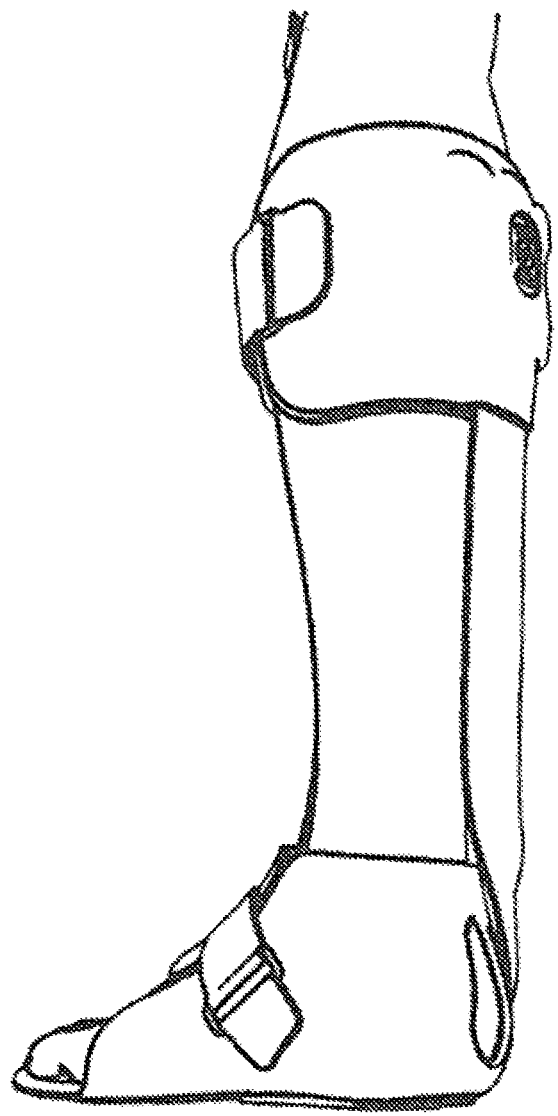
Figure 10:
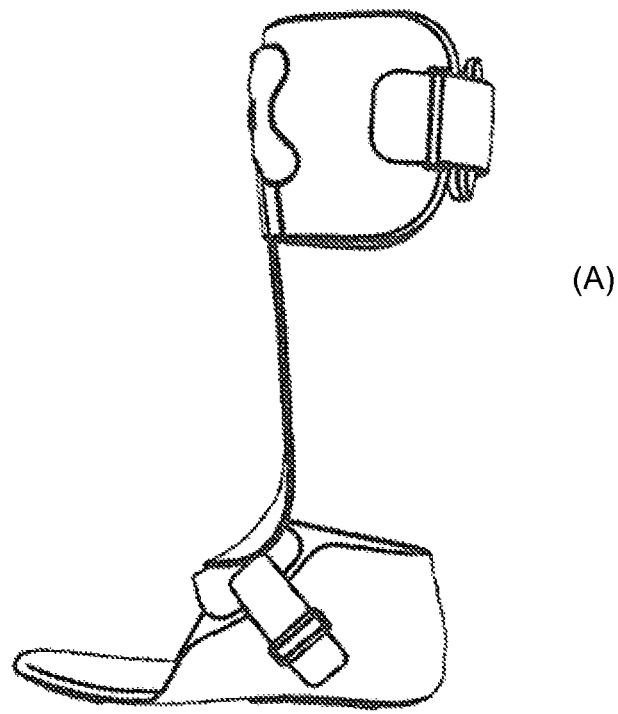
FIGS. 10(A) and 10(B) show an orthosis system according to the invention with ventral attachment of the lower-limb cuff.
Figure 10:
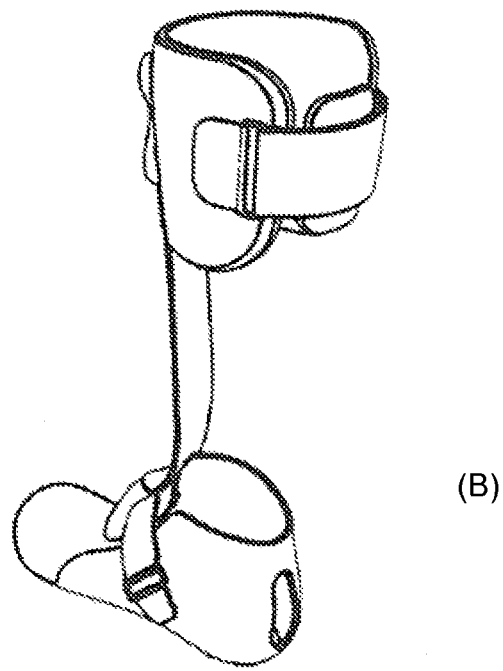

At its upper end, the backing spring is introduced into a corresponding opening of the lower-limb cuff and is screwed therewith. The details of this screwing are disclosed further below. At its lower end, it has a semicircular shape, in order to enclose the foot cuff. A peculiarity of the system according to the invention is that the enclosure of the foot cuff may be medial or lateral. Further, the backing spring may be disposed dorsally or ventrally. It is obvious to the person skilled in the art that in case of a change of the design of the orthosis according to the invention from ventral to dorsal mode, the lower-limb cuff needs to be rotated by 180° (see also FIG. 9 in comparison with FIG. 10). It is crucial for the system according to the invention that the backing spring can be prepared in different sizes, but also in different spring strengths (hardnesses). The different spring strengths can be achieved by different materials, different material thicknesses or also by targeted reinforcements (embedded rods, ribs, etc.). In this way, a selection of different backing springs can be tested with the patients, for instance after completed adjustment of foot and lower-limb cuff. The different types of wearing (medial und lateral, ventral und dorsal) as well as the different degrees of hardness (spring strengths) can immediately be compared to each other. In this way, patient and therapist can compare the patient's postural control and thus design the optimum orthosis.

Another essential aspect of the present invention is the attachment of lower-limb cuff and backing spring by clamping and screwing. With a rigid screw connection, as otherwise common, a relative movement between lower limb and lower-limb cuff will occur, when the patient moves, so that the generation of pressure sores and abrasions is possible. The system according to the invention comprises at this position a connection element, which acts by clamping and screwing. The nut is unidirectionally floating. For this purpose, this element contains an elastomer, which leads to a joint-type connection.

The central constituent of this connection element is preferably X-shaped ("starfish"). In a preferred embodiment of the invention, the lower-limb cuff includes a likewise X-shaped recess that is intended for receiving this connection element ("starfish"). The connection element ("starfish") consists of a rigid material and includes a recess. In the recess is fitted by form-fit a connection piece, which is made of an elastomer. By this flexible connection piece, the relative movements mentioned above are minimized. The elastomer can be prepared in different degrees of elasticity, so that the necessary damping of the relative movement can also be tested by tests on the patient.

Subject matter of the present invention, therefore, is also a kit for individually adjusting an orthosis, comprising
  a selection of different industrially pre-fabricated soles, a
    selection of different industrially pre-fabricated sandal-
    type foot cuffs, a selection of different industrially
    pre-fabricated lower-limb cuffs,
  a selection of different industrially pre-fabricated backing
    springs, and
  a selection of different paddings for the foot and lower-
    limb cuffs,
  a selection of different connection elements with different
    degrees of elasticity.

By that the modular orthosis system according to the invention contains only a few variable components, such a kit can be provided for the treating therapist and the assistant orthopedics technician, which kit respectively contains a series of variable components with different properties. After selection of the foot and lower-limb cuff (if applicable, after individual preparation of the foot cuff and lower-limb cuff, for instance using a plaster cast) a series of different pre-fabricated soles (with different heel heights or different degrees of hardness), different backing springs (for different styles of wearing and different lengths) and, if applicable, different connection elements with different degrees of elasticity can be provided for the treating therapist and the assistant orthopedics technician.

With the aid of the kit, the orthopedics technician or the therapist can individually perform the adjustment for every patient. Of particular importance is the selection of the correctly shaped sole and of the backing spring. The therapist can test, together with the patient, different spring strengths, but can also check the position of the backing spring (dorsally or ventrally, medially or laterally). In this way, the adjustment of the orthosis to the patient can be carried out in a simple manner.

For instance, a video recording of the postural control of the respective patient can be performed on a treadmill. The different postural control images can be shown side-by-side and allow the therapist to select the optimum movement posture, of course under consideration of the patient's individual wearing feeling. If the selection is optimized for height, spring strength, and wearing position, the therapist can assemble the individual components for the patient. In this way, a simple adjustment to the patient is possible.

The respective paddings are made of a breathable material, e.g., of washable, heat and humidity-transporting, air-permeable, hook-and-loop-fastenable ("Velcro") 3-D spacer fabric (e.g., Space Tex) that can be washed in the washing machine for instance at 30° C.

The sole and in particular the backing spring are prepared using materials making resilient and energy-storing components, such as, e.g., carbon fiber Prepreg.

A particular advantage of the orthosis system according to the invention is the possibility to dynamically adjust the orthosis, in particular in the growth phase of children and juveniles. The individual components and the protection element (bumper) may be configured differently on the outside, for instance by imprinting, engraving, or the like. In this way, the orthoses, in particular for children and juveniles, can be designed in an individualized manner, so that the acceptance of wearing is clearly improved.

The invention claimed is:

1. A modular production and adjustment system for orthoses, comprising:
   a thermally formed sole configured for mounting by reversible form-fit with one or a plurality of preformed receptacles for locking elements,
   a lower-limb cuff having:
      one or a plurality of fixing devices for fixing at a lower limb,
      a padding and a receiving device for a backing spring, wherein the backing spring includes an upper flat portion and a lower semicircular portion, the semicircular portion forming a recess for receiving the sole,
   wherein the backing spring is reversibly connected to the lower-limb cuff, and
   wherein the backing spring is configured to be attached dorsally/medially, dorsally, laterally, ventrally/medially, or ventrally/laterally at the a foot cuff.

2. The modular production and adjustment system for orthoses according to claim 1, wherein the reversible connection of lower-limb cuff and backing spring occurs by screwing with a unidirectional floating connection element.

3. The modular production and adjustment system according to claim 1, wherein a reversible connection of sole and backing spring occurs by clamping using the locking elements.

4. The modular production and adjustment system for orthoses according to claim 1, wherein the sole and/or backing spring and/or receiving device are made of pre-impregnated fiber support materials.

5. The modular production and adjustment system for orthoses according to claim 4, wherein the sole and/or backing spring and/or receiving device are made of PrePreg in carbon.

6. The modular production and adjustment system for orthoses according to claim 1, wherein the lower-limb cuff and/or foot cuff are made of a thermoplastic material.

7. The modular production and adjustment system for orthoses according to claim 1, wherein the backing spring is covered by form-fit with a soft protection element.

8. The modular production and adjustment system according to claim 1, wherein the padding of the lower-limb cuff is made of washable, heat and humidity-transporting, air-permeable, hook-and-loop-fastenable 3-D spacer fabric.

9. A kit for individually adjusting an orthosis, comprising:
   a selection of different industrially pre-fabricated soles,
   a selection of different industrially pre-fabricated sandal foot cuffs,
   a selection of different industrially pre-fabricated lower-limb cuffs,
   a selection of different industrially pre-fabricated backing springs,
   a selection of different paddings for the foot and lower-limb cuffs, and
   a selection of different connection elements with different degrees of elasticity.

10. A lower-limb orthosis, comprising:
   a thermally formed sole mounted by reversible form-fit with one or a plurality of preformed receptacles for locking elements,
   a lower-limb cuff with one or a plurality of fixing devices for fixing at the lower limb,
   a padding and a receiving device for a backing spring, wherein the backing spring includes an upper flat portion and a lower semicircular portion, the semicircular portion forming a recess for receiving the sole,
   wherein the backing spring is reversibly connected with the lower-limb cuff, and
   wherein the backing spring is configured to be attached dorsally/medially, dorsally, laterally, ventrally/medially, or ventrally/laterally at a foot cuff.

11. The modular production and adjustment system for orthoses according to claim 1, further comprising a sandal foot cuff having padding and fixing devices.

12. The modular production and adjustment system according to claim 11, wherein the padding of the foot cuff is made of washable, heat and humidity-transporting, air-permeable, hook-and-loop-fastenable 3-D spacer fabric.

13. The orthosis according to claim 10, further comprising a sandal foot cuff having padding and fixing devices.

* * * * *